(12) United States Patent
Lund et al.

(10) Patent No.: US 11,202,554 B2
(45) Date of Patent: Dec. 21, 2021

(54) HANDLE FOR AN ENDOSCOPE

(71) Applicant: AMBU A/S, Ballerup (DK)

(72) Inventors: Jesper Grøndahl Lund, Ballerup (DK); Michael Kappler Hansen, Vallensbæk (DK)

(73) Assignee: AMBU A/S, Ballerup (DK)

( * ) Notice: Subject to any disclaimer, the term of this patent is extended or adjusted under 35 U.S.C. 154(b) by 238 days.

(21) Appl. No.: 16/492,064

(22) PCT Filed: Mar. 7, 2018

(86) PCT No.: PCT/EP2018/055611
§ 371 (c)(1),
(2) Date: Sep. 6, 2019

(87) PCT Pub. No.: WO2018/162561
PCT Pub. Date: Sep. 13, 2018

(65) Prior Publication Data
US 2021/0275001 A1    Sep. 9, 2021

(30) Foreign Application Priority Data

| Mar. 8, 2017 | (DK) | .......................... PA 2017 70167 |
| Mar. 8, 2017 | (DK) | .......................... PA 2017 70168 |
| Mar. 21, 2017 | (DK) | .......................... PA 2017 70198 |

(51) Int. Cl.
*A61B 1/00*          (2006.01)

(52) U.S. Cl.
CPC ....... *A61B 1/00066* (2013.01); *A61B 1/00114* (2013.01)

(58) Field of Classification Search
None
See application file for complete search history.

(56) References Cited

U.S. PATENT DOCUMENTS

| 609,570 | A | 8/1898 | Bowden |
| 3,897,775 | A | 8/1975 | Furihata |
| 4,203,430 | A | 5/1980 | Takahashi |
| 4,483,326 | A | 11/1984 | Yamaka et al. |
| 4,566,437 | A | 1/1986 | Yamaguchi |

(Continued)

FOREIGN PATENT DOCUMENTS

| CN | 102 271 572 B | 12/2011 |
| CN | 302 561 2315 | 9/2013 |

(Continued)

OTHER PUBLICATIONS

Communication under Rule 71(3) EPC issued in EP 18716112.0, dated Jan. 13, 2021.

(Continued)

*Primary Examiner* — Timothy J Neal
(74) *Attorney, Agent, or Firm* — Faegre Drinker Biddle & Reath LLP

(57) ABSTRACT

A handle (2) for an endoscope (1), the handle (2) having a proximal end, a distal end, a front and a back, and the handle (2) including a gripping section (12) separated by a transition section (17) from an operation section (13). The gipping section (12) surface is provided with grooves. The gripping section has a cross-section with mirror symmetry and varying radius of curvature, with the minimum radius (r) of curvature at the front of the handle (2).

8 Claims, 6 Drawing Sheets

(56) References Cited

U.S. PATENT DOCUMENTS

| | | |
|---|---|---|
| 5,170,775 A | 12/1992 | Tagami |
| 5,179,934 A | 1/1993 | Nagayoshi et al. |
| 5,512,035 A | 4/1996 | Konstorum et al. |
| 5,888,192 A | 3/1999 | Heimberger |
| 5,976,075 A * | 11/1999 | Beane ............... A61B 1/00147 600/106 |
| 6,210,337 B1 | 4/2001 | Dunham et al. |
| 6,830,545 B2 | 12/2004 | Bendall |
| 8,790,250 B2 | 7/2014 | Petersen et al. |
| D719,651 S | 12/2014 | Hoffmann et al. |
| 9,737,203 B1 * | 8/2017 | Rosado ................... A61B 1/32 |
| 2001/0023313 A1 | 9/2001 | Ide |
| 2003/0212308 A1 | 11/2003 | Bendall |
| 2005/0131279 A1 | 6/2005 | Boulais et al. |
| 2007/0232858 A1 | 10/2007 | Macnamara et al. |
| 2007/0239311 A1 | 10/2007 | Gasparraj |
| 2007/0282167 A1 | 12/2007 | Barenboym et al. |
| 2008/0051694 A1 | 2/2008 | Kato |
| 2009/0036742 A1 * | 2/2009 | Watanabe ............... A61B 1/042 600/178 |
| 2010/0121147 A1 | 5/2010 | Oskin et al. |
| 2011/0009694 A1 * | 1/2011 | Schultz ............. A61B 1/00105 600/109 |
| 2011/0208002 A1 * | 8/2011 | Kish .................... A61B 1/0052 600/146 |
| 2011/0257477 A1 | 10/2011 | McWeeney |
| 2012/0016203 A1 * | 1/2012 | King ................ A61B 17/00008 600/204 |
| 2012/0130160 A1 * | 5/2012 | Borrye ..................... A61B 1/04 600/103 |
| 2012/0149982 A1 * | 6/2012 | Fonger ............... A61B 17/3415 600/114 |
| 2012/0220828 A1 | 8/2012 | Iwasaki |
| 2013/0137924 A1 | 5/2013 | Iwasaki et al. |
| 2015/0196193 A1 | 7/2015 | Kienzle et al. |
| 2016/0242637 A1 * | 8/2016 | Tydlaska ............ A61B 1/00101 |
| 2017/0251906 A1 | 9/2017 | Hatano |
| 2018/0296069 A1 | 10/2018 | Matthison-Hansen |

FOREIGN PATENT DOCUMENTS

| | | |
|---|---|---|
| CN | 104 382 551 A | 3/2015 |
| CN | 105 327 443 A | 2/2016 |
| CN | 205 758 497 U | 12/2016 |
| EP | 0447216 | 9/1991 |
| EP | 2 050 383 | 4/2009 |
| JP | 2003070727 | 3/2011 |
| WO | 2007/136894 A2 | 11/2007 |
| WO | WO 2010/066787 | 6/2010 |
| WO | WO 2010/066789 | 6/2010 |
| WO | WO 2013/071938 | 5/2013 |
| WO | WO 2013/099390 | 7/2013 |
| WO | WO 2013/071938 | 8/2014 |
| WO | WO 2014/127780 | 8/2014 |
| WO | WO 2016/188537 | 12/2016 |
| WO | WO2016188538 | 12/2016 |

OTHER PUBLICATIONS

Search Report for related Danish Patent Application No. 2017 70167, dated Jun. 2, 2017.

Search Report for related Danish Patent Application No. 2017 70167, dated May 2, 2017.

International Preliminary Report on Patentability received for PCT Patent Application No. PCT/EP2018/055611, dated Sep. 19, 2019, 8 pages.

International Search Report and Written Opinion in related PCT Application No. PCT/EP2018/055611, dated May 30, 2018.

Search Report in related Danish Application No. PA 2017 70198, dated Apr. 28, 2017.

Patkin, M., "A Check-List for Handle Design", 2001, Ergonomics Australia On-Line (http://ergonomics.uq.edu.au/eaol/handle.pdf).

Search Report in related Danish Application No. PA 2017 70168, dated Jun. 2, 2017, 6 pages.

English Translation and First Office Action in related Chinese application No. 201880014861.1, dated May 20, 2021, 8 pages.

* cited by examiner

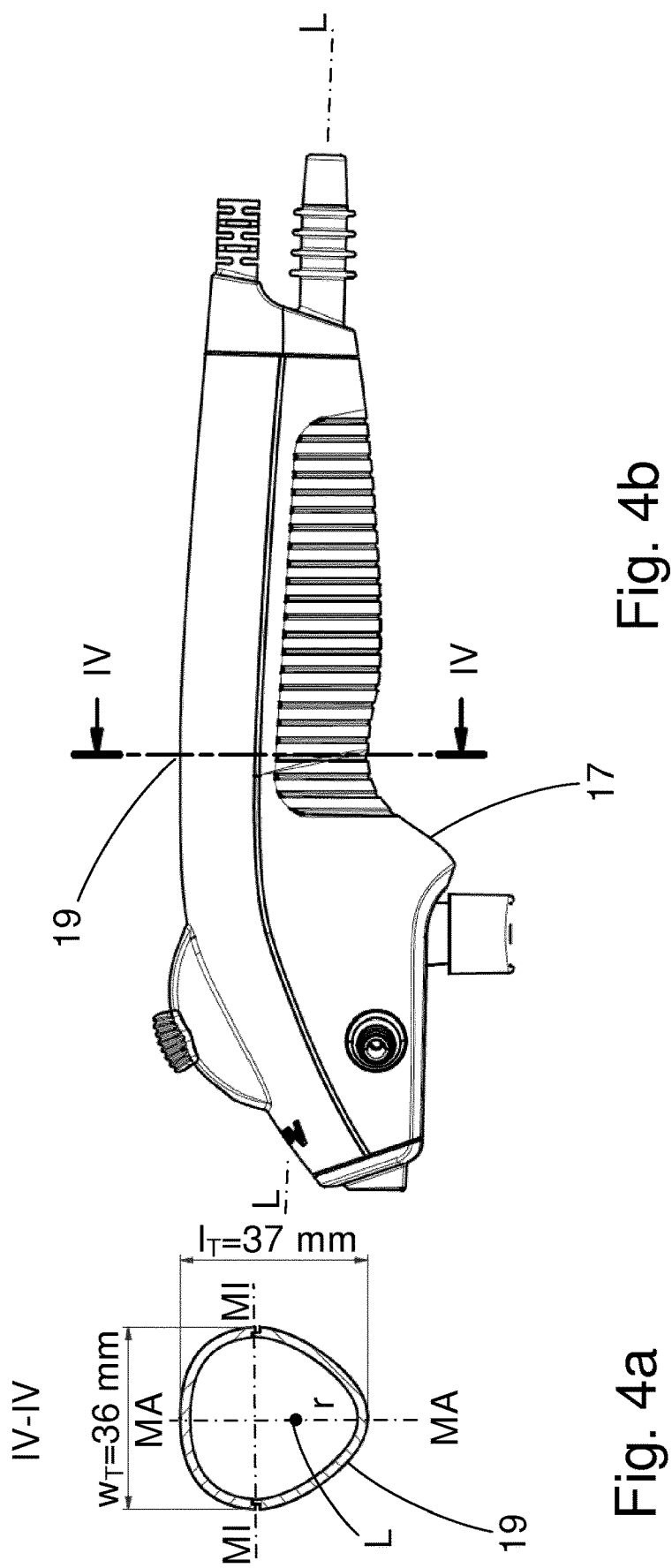

HANDLE FOR AN ENDOSCOPE

CROSS-REFERENCE TO RELATED APPLICATIONS

This application is a National stage application filed under 35 U.S.C. § 371 of International Application No. PCT/EP2018/055611, filed on Mar. 7, 2018, which claims the benefit of Denmark Patent Application No. PA 2017 70167, filed on Mar. 8, 2017, Denmark Patent Application No. PA 2017 70168, filed on Mar. 8, 2017, and Denmark Patent Application No. PA 2017 70198, filed on Mar. 21, 2017, which applications are incorporated herein by reference thereto.

TECHNICAL FIELD

The present invention relates to an endoscope and more specifically to a handle for an endoscope.

BACKGROUND OF THE DISCLOSURE

In general, an endoscope comprises an operating handle at the proximal end and an insertion tube extending from the handle towards the distal end. The handle is adapted to be held by an operator and inter alia comprises externally protruding operating members connected to internal control means allowing the operator to control the movement of a bending section at the distal end of the insertion tube, while advancing the distal end of the insertion tube to a desired location e.g. within a body cavity of a person. By means of an attached monitoring device, such as a monitor with a display screen, the location to which the distal end has been advanced may be inspected using the endoscope. Examples of such endoscopes are inter alia found in WO2013/071938 and WO2010/0696789. Advancing the distal end of the endoscope to a desired location may involve many bends and turns where the operator turns the handle about the general longitudinal axis of the insertion tube to bring the angular orientation of insertion tube, and hence the bending section, into a position from which the bending section may be bent to point towards a desired direction of view and/or of further advancement of the insertion tube. These many bends and turns requires complicated and often awkward movements of not only the hand or wrist of the operator, but also elbow, arm shoulder, and sometimes even the torso and legs of the operator, inter alia because the operator needs to keep his view on the monitor displaying the images from the camera at the distal tip of the endoscope. While doing so the only real references the operator has is a monitor with up and down directions defined by the camera at the tip of the distal end of the insertion tube. These directions, in turn, are linked to the handle to which the insertion tube is rigidly connected. During such movements the operator therefore needs to have a good and firm grip of the handle and a good sense of the current orientation of the handle, so as not to mentally loose the reference to the image viewed on the monitor, which is the operator's only immediate reference.

One such handle is found in applicant's own US design patent D719,651. This handle has been quite successfully implemented in the applicant's aScope™ 3 series of single-use endoscopes, but the applicant has realized that endoscope handles, in particular for single-use endoscopes, could be further improved in terms of the aforementioned grip and sense of orientation.

SUMMARY OF THE DISCLOSURE

Based on this, it is the object of the present invention to provide an ergonomically improved handle for an endoscope with better grip and sense of orientation.

According to a first aspect of the invention, this object is achieved by a handle for an endoscope, the handle having a proximal end, a distal end, a front and a back, and the handle comprising a gripping section separated by a transition section from an operation section, where the operating section comprises at least one protruding operating member adapted for operation by the thumb of the hand of the operator, the gripping section is adapted for being gripped by three or four fingers of a hand of an operator, the gripping section has an outer gripping section surface surrounding a longitudinal axis of the handle, where said outer gripping section surface defines a periphery with a predetermined curvature of cross-sectional gripping section shapes in a plane perpendicular to the longitudinal axis at points along the longitudinal axis, where said cross-sectional gripping section shapes vary along the longitudinal axis, and where the cross-sectional gripping section shapes are generally mirror symmetrical about a major axis defined by the intersection of the cross-sectional gripping section shape with a longitudinal plane coincident with the longitudinal axis, the operating section has an outer operating section surface surrounding a longitudinal axis of the handle, said outer operating section surface defines the periphery of cross-sectional operating section shapes in a plane perpendicular to the longitudinal axis at points along the longitudinal axis, where length of the periphery of a cross-sectional gripping section shape adjacent the transition section is smaller than the length of the periphery of a cross-sectional operating section shape adjacent the transition section, where the cross-sectional gripping section shapes are mirror asymmetrical about the minor axis defining the maximum width of the cross-sectional gripping section shape, where the radius of curvature of the periphery varies along the length thereof so as to present a minimum value at a radius coincident with the major axis at the front of the handle.

Providing the minimum radius at the front coincident with the major axis of the cross-section in this way conveys a highly improved sense of direction to the operator when gripping the handle and turning while viewing a stationary monitor.

According to a first preferred embodiment, the radius of curvature of the periphery of a cross-sectional gripping section shape varies along the length thereof so as to present a maximum value coincident with the major axis at the back of the handle. This further improves the sense of direction to the operator.

According to a second preferred embodiment, the length of the major axis at an intermediate cross-section taken between a cross-section at the distal end of the handle and a cross-section taken adjacent the transition section is larger than the length of the major axis of the cross-section taken adjacent the transition section. This not only improves the operators grip on the handle, but also makes it quite well defined, so as to further improve the operators sense of direction.

This may be further improved if according to a further embodiment the length of the major axis at an intermediate cross-section taken between a cross-section at the distal end of the handle and a cross-section taken adjacent the transition section is larger than the length of the major axis of the cross-section taken at the distal end of the handle.

According to yet a further embodiment, the minimum value of the radius of the curvature is less than 10 mm, preferably less than 9 mm. This has been found to be a good compromise between comfort, sense of direction conveyed, and provision of sufficient internal space in the endoscope handle.

Not all people are the like, but according to a preferred embodiment a length II of the major axis MA at the intermediate cross-section between 37 mm and 41 mm, has been found suitable for most people, while still taking into account the above mentioned comfort, sense of direction conveyed, and provision of sufficient internal space in the endoscope handle.

Likewise, according to further preferred embodiments, the length IT of the major axis MA at the cross-section taken adjacent the transition section is between 35 mm and 39 mm, and the length of the major axis MA at cross-section at the distal end is 35 mm or less. Preferably, the length II of the axis at the intermediate cross-section is larger than the length IT at the cross-section adjacent the transition section.

According to a specifically preferred embodiment, the gripping section comprises indentations, preferably a number of grooves, provided in the outer gripping section surface. This further improves the grip of the operator on the handle, in particular when the operator is having gel or the like on the gloves. This specific adaptation of the handle is highly advantageous in single-use endoscopes, because they need not be cleaned and sterilized, and having grooves in which gel and other contaminants might accumulate is of less concern.

According to a further preferred embodiment, the grooves extend in the circumferential direction of the gripping surface. This provides good grip in the insertion direction, where unlike the extraction direction and in the rotary direction the good grip is less supported by the overall shape of the handle.

According to a second aspect of the invention, this object is achieved by an endoscope with the handle according to the first aspect of the invention.

BRIEF DESCRIPTION OF THE DRAWINGS

The invention will now be described in greater detail based on non-limiting exemplary embodiments and with reference to the schematic drawings. In the drawings:

FIGS. 4a and 4b shows a cross-section and a side view, respectively, of the handle of FIG. 1, the cross-section being taken along the line IV-IV.

DETAILED DESCRIPTION

Figure 1:
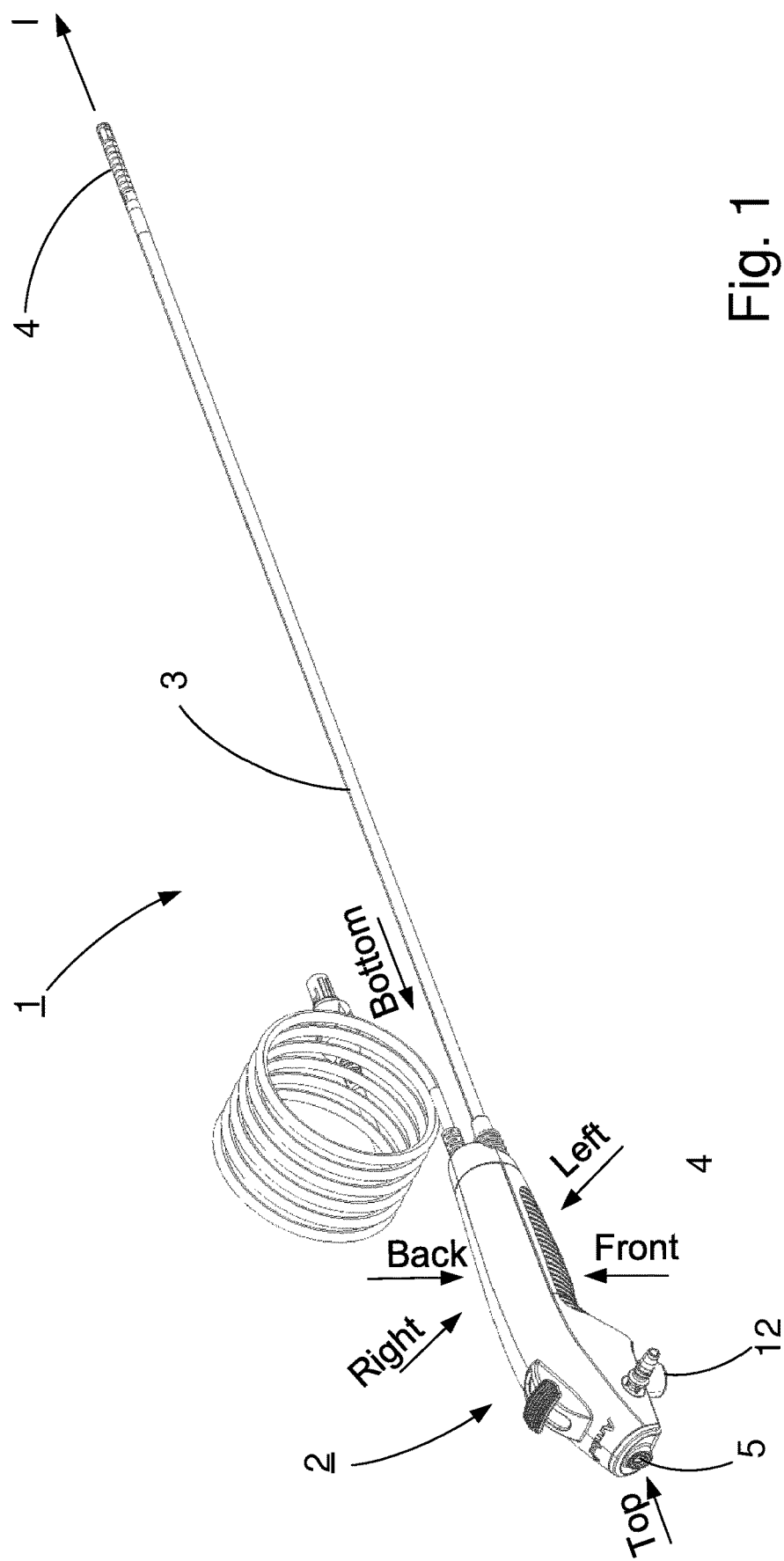
FIG. 1 shows a perspective view of an endoscope with a handle according to the invention.

Turning first to FIG. 1, an endoscope 1 with a handle 2 according to the present invention is shown. From the handle 2 the insertion tube 3 of the endoscope extends. If not influenced by any external forces the insertion tube 3 can be considered to be an essentially straight cylindrical body, the centre axis of which defines the longitudinal direction of the endoscope 1 and the handle 2 thereof from an articulated tip part 4 at the distal end to the proximal end where the handle 3 has an inlet port 5 for a working channel. This definition will be assumed throughout this description. Furthermore, for the definition of directions it will be assumed that the operator is standing in an upright position holding the endoscope in front of him with the distal end, i.e. the articulated tip part 4 of the insertion tube pointing downward, gripping the handle with three or four fingers, so that the operating knob 14 to be operated by his thumb protrudes towards him. Accordingly, for the purposes of understanding this invention and describing the endoscope 1 in general and the handle 2 in particular, the terms to define the main outer faces will be top, bottom, front, back, left-hand and right-hand as indicated in FIG. 1. Likewise, the directions away from these faces will be up, down, forward, backward, left and right.

Figure 2:
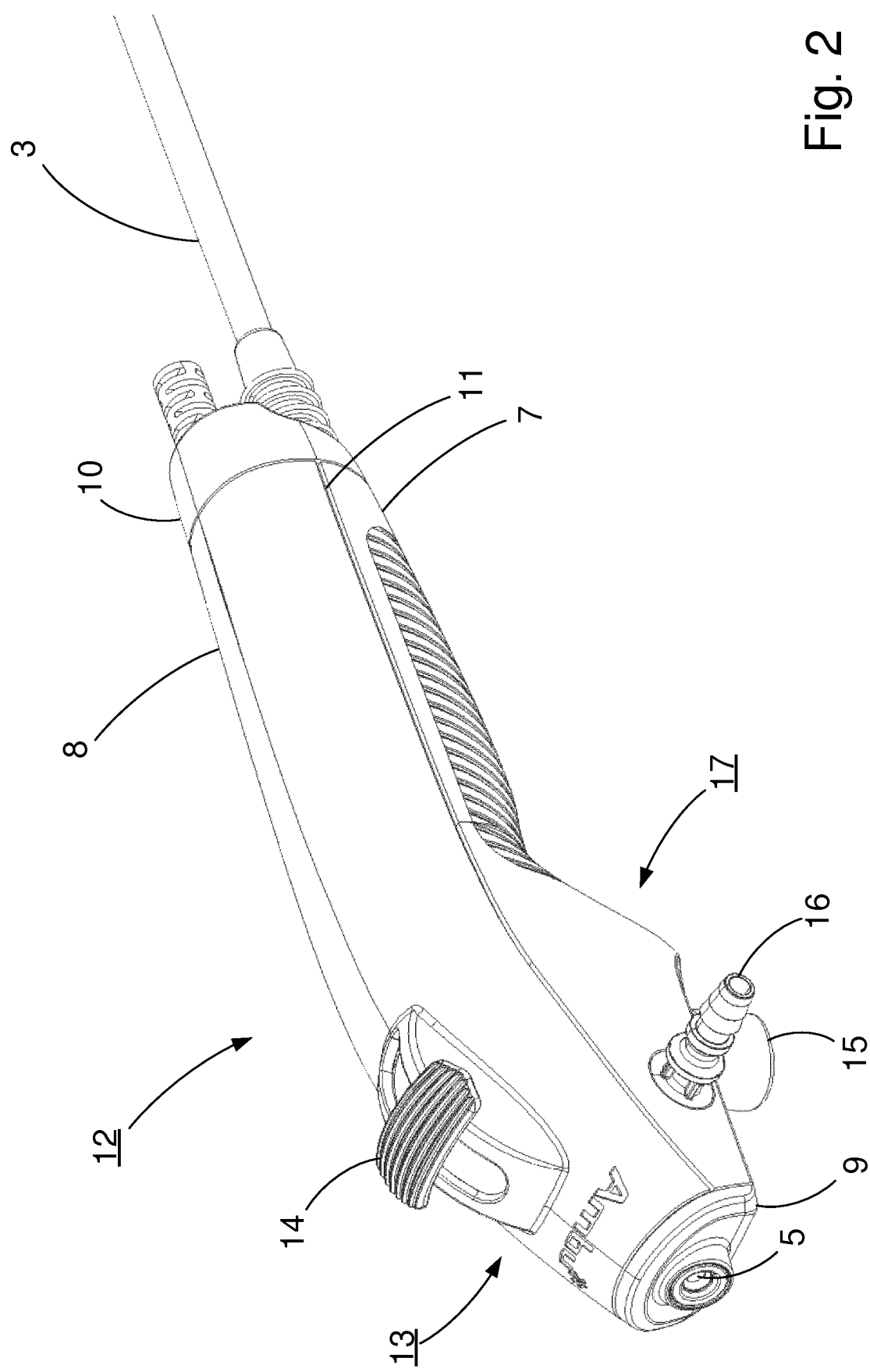
FIG. 2 shows an enlarged view of the handle of FIG. 1 in the same perspective.

Turning now to FIG. 2, the handle of FIG. 1 is shown in greater detail. The view corresponds to that of FIG. 1 and accordingly only the top, back and left-hand side of the handle 2 is visible. Please note that in FIG. 2 the cable 6 shown in FIG. 1 for connecting the endoscope 1 to external electronics, in particular the monitor on which the images form the camera in the tip of the endoscope 1 are shown, has been omitted for illustration purposes as it is not as such of relevance to the present invention.

The handle 2 comprises a housing which in the shown preferred embodiment comprises is made of four parts, namely a front shell part 7 a back shell part 8, a top closing part 9 and a bottom closing part 10. As will be understood by the skilled person from the following description, it is generally the shape of the handle housing which is important, rather than the actual number of parts chosen to form the housing. In this respect it should be noted that the skilled person will understand that when considering the shape of the handle housing, minor defects and deviations from an ideal shape, such as the groove 11 formed in the transition between the front shell part 7 and the back shell part 8 are joined, are negligible.

As can be further seen in FIG. 2 and other figures the handle 2 comprises two sections which in the following, without prejudice to actual use, are referred to as gripping section 12 and operating section 13. The gripping section 12 is adapted to be gripped and held by three or four fingers, more specifically the third to fifth digit of the hand of the operator, i.e. the operator's middle finger, ring finger, and little finger, and optionally also the second digit, i.e. the index finger. Adaptation to three or four fingers should in no way be understood mutually exclusive or even separate embodiment, but should rather be understood as one embodiment allowing for either, so that the operator can chose at will.

The operating section 13 comprises a protruding operating means such as a knob 14 adapted to be engaged by the thumb of the operator for actuation of the articulated bending section 4 of the endoscope 1 at the distal tip thereof, i.e. at the distal end of the insertion tube 3. The operating section 13 may optionally also comprise a push button 15 or the like for activating other functions of the endoscope 1, in particular a push button 15 for activation of suction, through a suction port 16 adapted to connect the endoscope 1 to the wall suction system normally found in hospitals and the like.

Between the gripping section 12 and the operation section 13 there is, in the preferred embodiment shown, a transition section 17.

Figure 3:
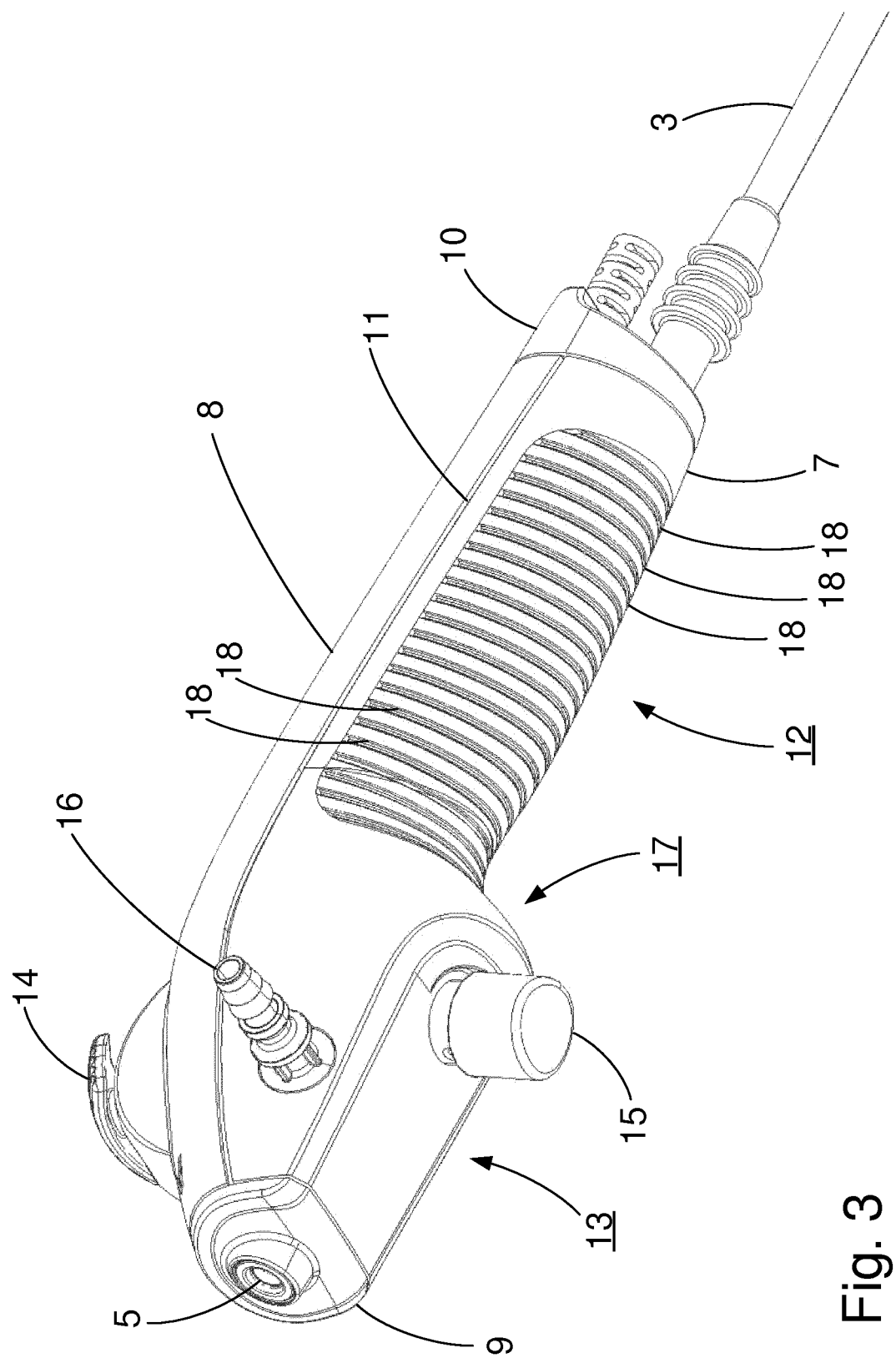
FIG. 3 shows another enlarged perspective view of the handle of FIG. 1.

The features of the handle 2 mentioned above in conjunction with FIG. 2 may also be seen in FIG. 3 showing the handle from a different perspective view in which the front of the gripping 12 section is better visible. As can be seen, the outer surface of the gripping section has been provided with indentations in the form of a number of grooves 18. These grooves 18 are approximately ½-1 mm wide and about the same in depth. The grooves 18 are preferably arranged side by side of each from the right-hand side to the left-hand side of the front shell part 7 (or vice versa), with a spacing from one groove 18 to the next of approximately 2-3 mm. The grooves 18 all preferably run transversely to the longitudinal direction of the handle 2, i.e. in the circumferential direction, but other directions are not excluded. The grooves 18 could run along the handle in the longitudinal direction, or across in an oblique angle, or combinations thereof. In the latter case forming a pattern of intersecting grooves 18. Grooves 18 running transversely as illustrated is however currently preferred, as they provide the most friction in the insertion direction I of the endoscope, as well as in the extraction direction. The latter is however of lesser importance, as in that case the gripping hand of the operator will normally abut the transition section 17 and thereby be prevented from slipping. This does however not exclude that the transition section may, at least in the abutment area, also be provided with grooves 18. The groves 18 are provided in an area with a length corresponding largely to the total width of second to fifth finger of a hand, i.e. approximately 80 mm along the length of the handle 2. As will be described later the shapes of cross-sections of the gripping portion 12 will aid in preventing the hand from slipping when turning the endoscope 1. Furthermore, grooves 18 are preferred over other indentations, e.g. dimples or the like, because the grooves 18 will serve to drain gel or the like between the operator's gloved hand and the gripping section 12 thereby reducing any lubricating effect of the gel or like, that could promote slipping. The fact that gel or the like including contaminants will enter the grooves 18 and residues thereof remain, is not a problem, in the case when the endoscope 1 for which the handle 2 is being used is a single-use endoscope. Being a single-use endoscope 1, meaning that the endoscope 1 is not to be used on another patient but disposed of, the need for cleaning and sterilizing the grooves 18 is obviated, therefore making the provision of the grooves 18 a substantial advantage over multiple-use endoscopes, where such grooves would make cleaning between usage more challenging.

Figures 5A, 5B:
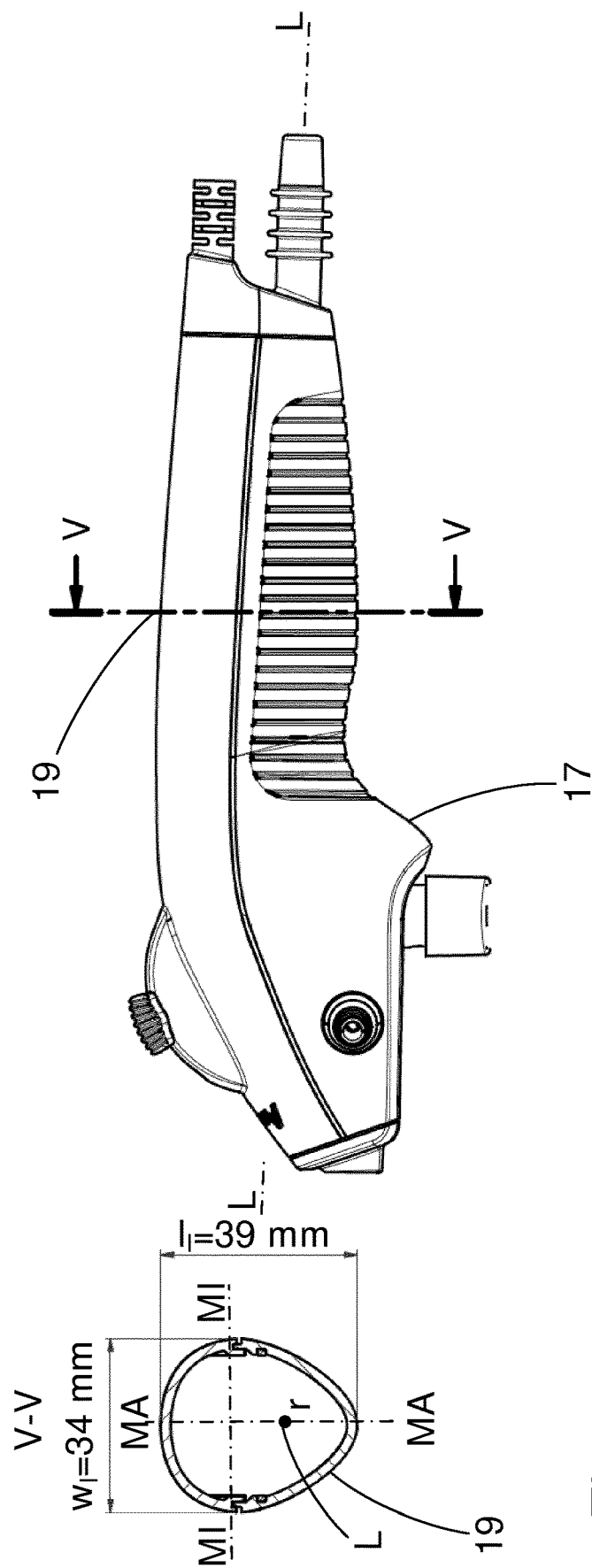
FIGS. 5a and 5b shows a cross-section and a side view, respectively, of the handle of FIG. 1, the cross-section being taken along the line V-V.
Figures 6A, 6B:
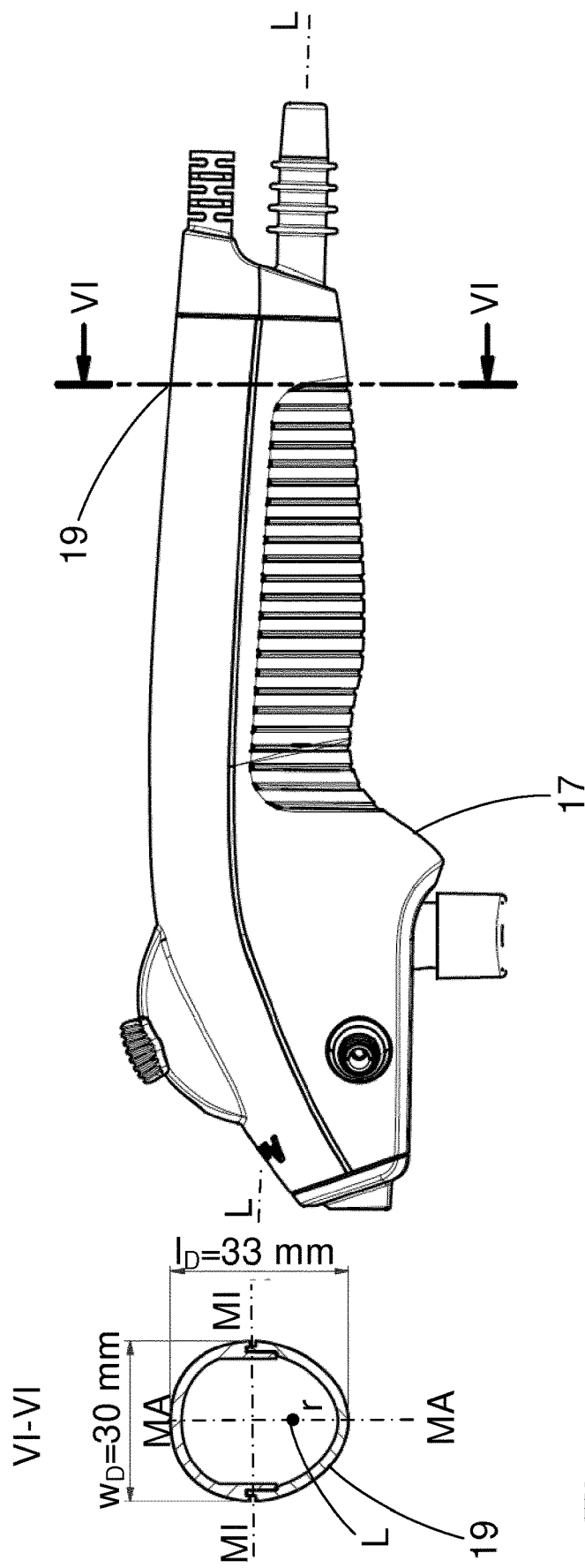
FIGS. 6a and 6b shows a cross-section and a side view, respectively, of the handle of FIG. 1, the cross-section being taken along the line VI-VI.

Turning now to FIGS. 4*b*, 5*b*, 6*b* identical side views from the left-hand side of the handle 2 for the endoscope 1 are shown. The side views differ only in the indication of where the respective cross-sections shown in FIGS. 4*a*, 5*a*, 6*a* are taken, i.e. along the lines IV-IV, V-V, VI-VI respectively.

Turning first to FIG. 4*a*, a cross-section IV-IV through the outer gripping section surface 19 provided by the housing 2 at a location adjacent or close to the transition section 17, is shown. The outer gripping section surface 19 surrounds a longitudinal axis L of the handle 2. The cross-section IV-IV shown is thus perpendicular to the longitudinal axis L. The cross-section IV-IV of the gripping section surface 19 defines a periphery of a generally oval shape, in particular an egg oval shape with a pointed end and a more rounded end, not unlike the shape known from many bird's eggs. The periphery thus has a curvature with a varying radius r of curvature. As can be seen, the oval shape of the periphery is generally mirror symmetrical about the axis MA, in the following referred to as the major axis of the oval. As can also be seen, the minimum radius r of curvature coincides with the major axis at the bottom of FIG. 4*a*, i.e. the front of handle 2. This minimum radius in FIG. 4*a* could be in the range 9-11 mm, preferably 10 mm or approximately 10 mm.

As will be explained later, this mirror symmetry extends along the gripping section 13, so as to define a plane in which both the longitudinal axis L and the major axis MA lie. That is to say a longitudinal symmetry plane intersecting the cross-section IV-IV and coincident with the longitudinal axis L. The symmetry allows the operator to use or grip the handle 2 of the endoscope 1 with either the left hand or the right hand as the operator pleases, when using it.

The length IT of the major axis MA at IV-IV is preferably in the interval between 35 mm and 39 mm preferably approximately 37 mm.

In a corresponding manner, FIG. 6*a* shows a cross-section VI-VI through the outer gripping section surface 19 provided by the housing 2 at a location adjacent distal end of the handle 2. Accordingly, also here the outer gripping section surface 19 surrounds the longitudinal axis L of the handle 2 and the cross-section VI-VI shown is perpendicular to the longitudinal axis L. As can be seen, also the cross-section IV-IV of the gripping section surface 19 defines a periphery of a generally oval shape, in particular an egg oval shape with a pointed end and a more rounded end, although the rounded end is more rounded and the pointed end is less pointed than at the cross-section IV-IV, but still with the minimum radius r of curvature coinciding with the major axis at the front of handle 2. This minimum radius in FIG. 6*a* could be in the range 11-13 mm, preferably 12 mm or approximately 12 mm. The periphery has a curvature with a varying radius r of curvature, which varies in a manner different from that of the cross-section IV-IV. Also this oval shape of the periphery is generally mirror symmetrical about the major axis MA, i.e. the longitudinal symmetry plane intersecting the cross-sections IV-IV and VI-VI and coincident with the longitudinal axis L.

The length ID of the major axis MA at VI-VI is preferably 35 mm or less, preferably approximately 33 mm.

Still in a corresponding manner, FIG. 5*a* shows a cross-section V-V through the outer gripping section surface 19 provided by the housing 2 at a location intermediate the transition section 17 and the distal end of the handle 2. Also here, the outer gripping section surface 19 surrounds the longitudinal axis L of the handle 2 and the cross-section V-V shown is perpendicular to the longitudinal axis L. Also here the cross-section V-V of the gripping section surface 19 defines a periphery of a generally oval shape, in particular an egg oval shape with a pointed end and a more rounded end, although the rounded end is less rounded and the pointed end is more pointed than at the cross-sections IV-IV and VI-VI, but still with the minimum radius r of curvature coinciding with the major axis at the front of handle 2. Accordingly, the periphery has a curvature with a varying radius r of curvature, which varies in a manner different from those of the cross-sections IV-IV and VI-VI, but still the oval shape of the periphery is generally mirror symmetrical about the major axis MA, i.e. the longitudinal symmetry plane intersecting the cross-sections IV-IV and VI-VI and any cross-sections in between, such as the cross-section V-V, and coincident with the longitudinal axis L. Apart from giving the sense of direction, these egg ovals shapes also prevent rotary slipping of the handle 2 in the hand of the user when the pointed ends lie in the middle interphalangeal digital creases of the operators hand.

At this intermediate section V-V the length II of the major axis MA has its maximum value among all cross-sections perpendicular to the longitudinal axis L between the cross-section IV-IV at the transition section 17 and the cross-section VI-VI at the distal end. This provides the gripping surface 19 with the profile readily visibly in any of the FIG. 4*b*, 5*b* or 6*b*, where a hump or hogback is formed between the distal end and the transition section 17. The length IT of the major axis MA at IV-IV is preferably in the interval between 35 mm and 39 mm preferably approximately 37 mm. Neglecting the variations from the grooves 18 it can be seen that the length of the major axes MA of the cross-sections decrease more rapidly from the cross-section V-V towards the local minimum at cross-section IV-IV in the direction towards transition section 17 than in the opposite direction towards the distal end of the handle 2.

Preferably, the minimum radius r of curvature at the cross-section V-V is also preferably the minimum value of all radii r of curvature of all cross-sections perpendicular to the axis L between the cross-section VI-VI at the distal end to the cross-section IV-IV at the transition section 17, making the hogback more pronounced and improving the sense of direction to the operator gripping the handle 2 at the gripping section 12 as well as the rotary slippage prevention. This minimum value of the radius r is preferably less than 10 mm, more preferred less than 9 mm.

Preferably, the minimum radius r of curvature at the cross-section VI-VI (see FIG. 6*b*) is larger than the minimum radius r of curvature at the cross-section IV-IV (see FIG. 4*b*).

By further comparison of FIGS. 4*a*, 5*a* and 6*a* it will be apparent that also the maximum width of the handle 2 varies along the length thereof. Unlike the front-to-back dimensions along the major axes MA, the width varies continuously, increasing constantly from the distal end of endoscope 1 to the transition section 17. The location of the maximum width is referred to as the minor axis MI extending orthogonally to the major axis MA, as can be seen in any of FIG. 4*a*, 5*a* or 6*a*. As can also be seen, the intersections of the major axes MA with the minor axes MI need in no way coincide with the longitudinal axis L.

The maximum width of the gripping section 12 is thus found adjacent the transition section 17. At the cross-section IV-IV, the width wT, i.e. the length of the minor axis MI is more or less the same as the length of the major axis MA, but as can be seen the cross-section IV-IV is far from circular. Preferably the length wT of the minor axis MI is between 34 mm and 38 mm, more specifically approximately 36 mm. At the cross-section V-V where the length of the major axis MA has its maximum value along the part of the gripping section 12 located between cross-sections IV-IV and VI-VI, the length of the minor axis wl is preferably between 32 mm and 36 mm, more specifically approximately 34 mm, the egg oval shape thus being more oblong as compared with the one at cross-section IV-IV.

At the distal end of the gripping section 12 the width is even smaller. At the cross-section VI-VI where the area provided with the grooves 18 ends, the width wD is preferably between 28 mm and 32 mm more specifically approximately 30 mm.

As may be seen from FIG. 2 the width of the handle 2 continues to increase through and past the transitions section 17 into the operating section 13 before it narrows down again towards the proximal end of the endoscope 1 at the top closing part 9. This provides good space for the parts accommodated within the operating section. However, as in the preferred embodiment the operator should be able to reach and push the push-button 15 with sufficient force with his index finger the maximum possible width of the operating section is limited. Preferably the maximum width of the operating section 13 is between 36 mm and 40 mm, more specifically approximately 38 mm.

With the endoscope 1 and handle 2 as described above an improved endoscope 1 is provided, and especially an improved single-use endoscope 1. It should be noted, however, that the invention is not limited to the specific exemplary embodiment disclosed. Rather, within the limitations of the claims numerous other embodiments and variants are possible.

We claim:
1. A handle for an endoscope, the handle comprising:
a proximal end, a distal end, a front and a back, a gripping section, an operating section, and a transition section, the gripping section being separated from the operating section by the transition section,
wherein the operating section comprises at least one protruding operating member adapted for operation by a thumb of a hand of an operator, the gripping section is adapted for being gripped by three or four fingers of the hand of the operator, and the gripping section has an outer gripping section surface surrounding a longitudinal axis of the handle,
where said outer gripping section surface defines a periphery with a predetermined curvature of cross-sectional gripping section shapes in a plane perpendicular to the longitudinal axis at points along the longitudinal axis, and where said cross-sectional gripping section shapes vary along the longitudinal axis,
where each cross-sectional gripping section shape is generally mirror symmetrical about a major axis defined by the intersection of the cross-sectional gripping section shape with a longitudinal plane coincident with the longitudinal axis,
where the operating section has an outer operating section surface surrounding the longitudinal axis of the handle, said outer operating section surface defines a periphery of the cross-sectional operating section shapes in a plane perpendicular to the longitudinal axis at points along the longitudinal axis,
where the length of the periphery of a cross-sectional gripping section shape adjacent the transition section is smaller than the length of the periphery of a cross-sectional operating section shape adjacent the transition section,
where each cross-sectional gripping section shape is mirror asymmetrical about a minor axis, the minor axis defining a maximum width of the cross-sectional gripping section shape, and
where the radius of curvature of the periphery of each cross-sectional gripping section shape varies along the length thereof from a proximal cross-section, adjacent the transition section, to an intermediate cross-section to a distal cross-section so as to present a minimum value at a radius coincident with the major axis at the front of the handle,
wherein the minimum value of the radius of curvature is between 9-11 mm at the proximal cross-section, less than 10 mm at the intermediate cross-section, and between 11-13 mm at the distal cross-section; and
wherein the length of the major axis is between 35 mm and 39 mm at the proximal cross-section, between 37 mm and 41 mm at the intermediate cross-section, and 35 mm or less at the distal cross-section.
2. The handle of claim 1, wherein the radius of curvature of the periphery of each cross-sectional gripping section shape varies along the length thereof so as to present a maximum value coincident with the major axis at the back of the handle.

3. The handle of claim 2, wherein the length of the major axis at an intermediate cross-section taken between a cross-section at the distal end of the handle and a cross-section taken adjacent the transition section is larger than the length of the major axis of the cross-section taken adjacent the transition section.

4. The handle of claim 1, wherein the handle is configured for single-use, and wherein the gripping section comprises a plurality of parallel grooves.

5. An endoscope comprising the handle of claim 1.

6. The endoscope of claim 5, wherein the radius of curvature of the periphery of each cross-sectional gripping section shape varies along the length thereof so as to present a maximum value coincident with the major axis at the back of the handle.

7. The endoscope of claim 6, wherein the length of the major axis at an intermediate cross-section taken between a cross-section at the distal end of the handle and a cross-section taken adjacent the transition section is larger than the length of the major axis of the cross-section taken adjacent the transition section.

8. The endoscope claim 5, wherein the handle is configured for single-use, and wherein the gripping section comprises a plurality of parallel grooves.

\* \* \* \* \*